US00PP18355P2

(12) United States Plant Patent
Koppe

(10) Patent No.: US PP18,355 P2
(45) Date of Patent: Dec. 25, 2007

(54) *BEGONIA* PLANT NAMED 'BERSEKO LIGHT PINK'

(50) Latin Name: *Begonia×hiemalis*
Varietal Denomination: Berseko Light Pink

(75) Inventor: Lubbertus H. Koppe, Ermelo (NL)

(73) Assignee: Koppe Royalty B.V., Ermelo (NL)

( * ) Notice: Subject to any disclaimer, the term of this patent is extended or adjusted under 35 U.S.C. 154(b) by 0 days.

(21) Appl. No.: 11/489,328

(22) Filed: Jul. 19, 2006

(51) Int. Cl.
*A01H 5/00* (2006.01)

(52) U.S. Cl. ..... Plt./343

(58) Field of Classification Search ..... Plt./343
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Begonia* plant named 'Berseko Light Pink', characterized by its compact, upright and mounded plant habit; freely branching habit; double flowers that are light pink in color and held above the foliage; and excellent postproduction longevity.

1 Drawing Sheet

Botanical designation: *Begonia×hiemalis.*
Cultivar denomination: 'Berseko Light Pink'.

BACKGROUND OF THE INVENTION

The present invention relates to a new and distinct cultivar of *Begonia* plant, botanically known as *Begonia×hiemalis,* commercially known as Elatior Begonia, and hereinafter referred to by the name 'Berseko Light Pink'.

The new *Begonia* was discovered by the Inventor in a controlled environment in Ermelo, The Netherlands, in December, 2002, as a naturally-occurring whole plant mutation of *Begonia×hiemalis* cultivar Berseko, not patented. The new *Begonia* was observed as a single plant in a group of flowering plants of the parent cultivar. The selection of this plant was based on its flower coloration.

Asexual reproduction of the new *Begonia* by cuttings in a controlled environment in Ermelo, the Netherlands since June, 2004, has shown that the unique features of this new *Begonia* are stable and reproduced true to type in successive generations.

SUMMARY OF THE INVENTION

The cultivar 'Berseko Light Pink' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Berseko Light Pink'. These characteristics in combination distinguish 'Berseko Light Pink' as a new and distinct *Begonia:*

1. Compact, upright and mounded plant habit.
2. Freely branching habit.
3. Double flowers that are light pink in color and held above the foliage.
4. Excellent postproduction longevity.

Plants of the new cultivar are most similar to plants of the parent, the cultivar Berseko. Plants of the new cultivar differ primarily from plants of the cultivar Berseko in flower color as plants of the cultivar Berseko have darker pink-colored flowers.

Plants of the new *Begonia* can also be compared to plants of the cultivar Bina, not patented. In side-by-side comparisons conducted in Ermelo, The Netherlands, plants of the new *Begonia* differed from plants of the cultivar Bina in the following characteristics:

1. Plants of the new *Begonia* were more freely branching than plants of the cultivar Bina.
2. Plants of the new *Begonia* had brighter pink-colored flowers than plants of the cultivar Bina.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the top of the sheet comprises a side perspective view of a typical flowering plant of 'Berseko Light Pink' grown in a container.

The photograph at the bottom of the sheet is a close up view of typical flowers and leaves of 'Berseko Light Pink'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in Ermelo, The Netherlands, under commercial practice in a glass-covered greenhouse during the spring and summer. Average day and night temperature was about 20°

C. during the first three to four weeks then lowered to an average day and night temperature of 18° C. until flowering. Four weeks after planting rooted cuttings in 12-cm containers, one week of long nyctoperiods of 16 hours was given followed by short nyctoperiods of eight hours until flowering. Plants used for the photographs and the description were about 15 weeks from planting.

Botanical classification: *Begonia×hiemalis* cultivar 'Berseko Light Pink'.

Commercial classification: Elatior Begonia.

Parentage: Naturally-occurring whole plant mutation of *Begonia×hiemalis* cultivar Berseko, not patented.

Propagation:

*Type.*—By terminal vegetative cuttings.

*Time to develop roots.*—About 20 days at temperatures 20° C.

*Time to produce a rooted young plant.*—About 42 days at temperatures of 20° C.

*Root description.*—Fine, fibrous, well-branched; white/orange in color. Plants of the new *Begonia* have not been observed to form tubers.

Plant description:

*Plant form.*—Compact, upright and mounded plant habit, inverted triangle; freely branching with good stem and stem base strength. Flowers are double and abundant. Plants flower continuously.

*Growth habit.*—Moderate growth rate, vigorous. Suitable for 11 to 15-cm containers. Under optimal environmental and cultural conditions, usually about 15 weeks are required to produce proportional 14-cm potted plants from cuttings. Vegetative shoots are formed at basal nodes and flowering shoots are formed at upper nodes.

*Plant height.*—About 20 cm to 25 cm.

*Plant width.*—About 35 cm.

*Leaves.*—Arrangement: Simple, alternate. Developing leaves, length: About 4 cm to 5 cm. Developing leaves, width: About 6 cm to 7 cm. Fully expanded leaves, length: About 11 cm to 14 cm. Fully expanded leaves, width: About 13 cm to 15 cm. Shape: Roughly reniform. Apex: Acute. Base: Cordate. Margin: Doubly serrate. Texture, upper surface: Smooth, glabrous; margins, pubescent. Texture, lower surface: Slightly pubescent. Venation pattern: Palmate. Color: Developing leaves, upper surface: 137A. Developing leaves, lower surface: 191A to 191B. Fully expanded leaves, upper surface: 147A; venation, close to 146D. Fully expanded leaves, lower surface: 191A; venation, close to 146D. Petiole length: About 1 cm to 8 cm. Petiole texture, upper and lower surfaces: Pubescent. Petiole color, upper and lower surfaces: 178C to 178D.

Flower description:

*Flowering habit.*—Double flowers with numerous tepals arranged in axillary cymes. Usually six to ten flowers per cyme. Many cymes in flower simultaneously. Flowers positioned above the foliage. Flowering continuous.

*Natural flowering season.*—Plants will flower year round regardless of nyctoperiod, however plants flower earlier and more abundantly from mid-February until November in the Northern Hemisphere.

*Flowers.*—Shape: Rounded; rose-like. Diameter: About 5 cm to 8 cm. Depth (height): About 2 cm to 3 cm.

*Flower buds.*—Length: About 1.5 cm to 2.2 cm. Diameter: About 1.6 cm to 2.6 cm. Color: Close to 52D.

*Tepals.*—Arrangement: Rosette. Quantity per flower: Usually about 30 per flower. Size: Outer tepals, length: About 3.3 cm to 4 cm. Outer tepals, width: About 3.4 cm to 4.4 cm. Inner tepals, length: About 1.4 cm to 2.2 cm. Inner tepals, width: About 1.1 cm to 2 cm. Shape: Rounded flabellate. Apex: Rounded. Margin, outer and inner tepals: Slightly crenate. Texture, upper and lower surfaces: Smooth, glabrous; satiny. Color: When opening, upper and lower surfaces: Slightly darker than 62A. Fully opened, upper surface: Slightly lighter than 62A. Fully opened, lower surface: Close to 54C.

*Flower bracts.*—Quantity/arrangement: Two, opposite. Shape: Broadly cordate. Apex: Acute. Margin: Serrate. Texture, upper and lower surfaces: Glabrous, smooth. Color, upper and lower surfaces: 144B overlain with close to 183A.

*Peduncles.*—Angle: Erect. Length: About 4 cm to 7 cm. Texture: Slightly pubescent. Color: Close to 146C.

*Pedicels.*—Angle: Erect. Length: About 8 mm to 4 cm. Texture: Pubescent. Color: More red than 161B.

*Reproductive organs.*—Stamens: None observed. Pistils: None observed.

*Seed/fruit.*—Seed and fruit production have not been observed as reproductive organs are not formed.

Postproduction longevity:

*Individual flowers.*—Generally about two to three weeks.

*Whole plants.*—About six weeks under interior conditions.

Disease/pest resistance: Resistance to pathogens and pests common to *Begonia* has not been observed.

Temperature tolerance: Plants of the new *Begonia* have been observed to tolerate temperatures from about 10° C. to about 35° C.

It is claimed:

1. A new and distinct *Begonia* plant named 'Berseko Light Pink' as illustrated and described.

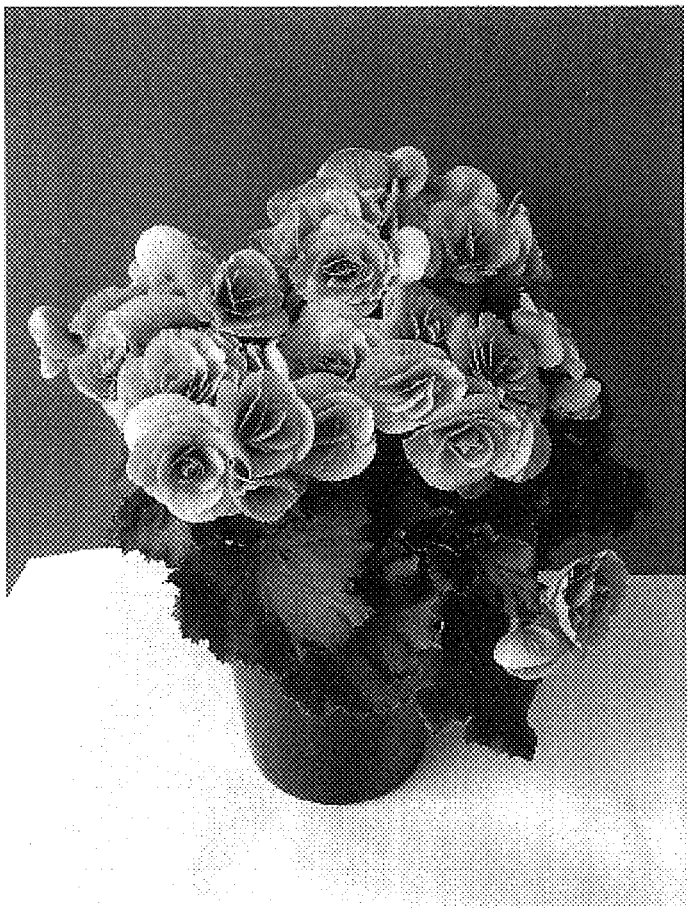
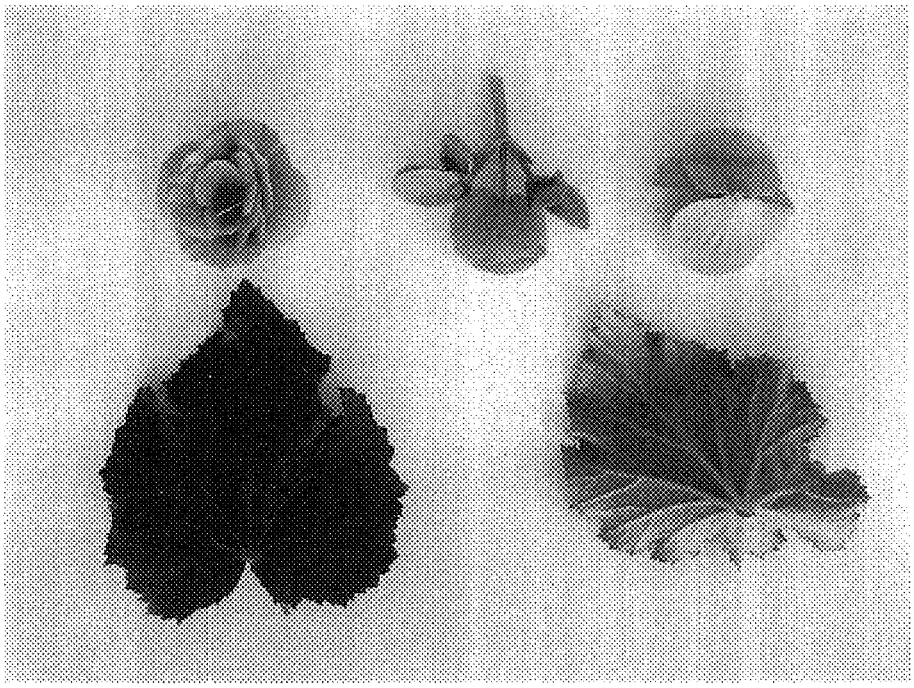

* * * * *